United States Patent [19]

Goodman

[11] Patent Number: 4,980,364

[45] Date of Patent: Dec. 25, 1990

[54] METHOD OF DECONGESTING THE NOSE WITHOUT ADVERSE STIMULANT EFFECTS

[76] Inventor: Robert M. Goodman, 1402 Astor Ave., Bronx, N.Y. 10469

[21] Appl. No.: 371,531

[22] Filed: Jun. 26, 1989

[51] Int. Cl.$^5$ ............................................. A61K 31/42
[52] U.S. Cl. ................................................... 514/377
[58] Field of Search ........................................ 514/377

[56] References Cited

U.S. PATENT DOCUMENTS 3,161,650  12/1964  Poos ..................................... 548/234

4,256,755  3/1981  Smith, Jr. ............................. 514/377

OTHER PUBLICATIONS

Chem. Abst., 83:91037v, (1975), Engelhardt et al.

*Primary Examiner*—Stanley J. Friedman
*Assistant Examiner*—Zohreh A. Fay

[57] ABSTRACT

Disclosed is the use of (+/−)-cis-2-amino-4-methyl-5-phenyl-2-oxazoline as a nasal decongestant which, when administered orally, does not produce adverse central nervous system stimulant effects as experienced with other decongestants and anorexiants.

5 Claims, No Drawings

METHOD OF DECONGESTING THE NOSE WITHOUT ADVERSE STIMULANT EFFECTS

BACKGROUND OF THE INVENTION

Alpha adrenergic agonists have long been used advantageously for their vasoconstrictor effect in decongesting the nose and paranasal sinuses. However, such agonists share with other sympathomimetic agents some degree of stimulation of the central nervous system. Some of the effects are perceived as quite adverse, and limit the usefulness of such materials when administered systemically. Topical administration via nose spray or drops avoids these problems in most cases, but is not effective in decongesting the sinuses. The present invention employs an alpha adrenergic agonist which when administered systemically is an effective nasal and sinus decongestant, but does not produce the adverse stimulant effects associated with common sympathomimetic substances.

BRIEF SUMMARY OF THE INVENTION

A compound called 2-amino-4-methyl-5-phenyloxazoline (see below for other names) was disclosed as Example IV in U.S. Pat. No. 3,161,650 by George I. Poos. The object of that invention had been development of central nervous system stimulants, in the hope that some of them would prove not to have some of the adverse effects associated with others of that class. Some of the invented compounds were also shown to have anorexiant activity.

The present invention consists of the oral administration of 0.25 mg of 2-amino-4-methyl-5-phenyloxazoline per kg of human body weight to decongest the nose and paranasal sinuses for at least 12 hours. In contrast to pseudoephedrine and phenylpropanolamine administration, the present invention does not produce, for a comparable decongestant effect, adverse effects mimicking anxiety.

DETAILED DESCRIPTION

For treatment of his allergic rhinitis and asthma, the present inventor has had considerable experience with sympathomimetic drugs. For bronchodilation these have included the beta adrenergic agonists albuterol, ephedrine, and theophylline. For nasal and sinus decongestion these have included the alpha adrenergic agonists pseudoephedrine and phenylpropanolamine (norephedrine). Effective doses of any of these produce noticeable central nervous system stimulation in me.

This CNS stimulation has two major classes of effects. The first is general stimulation, resulting in increased activity and arousal. This class is not necessarily adverse, except when wakefulness is inconvenient.

The second class of CNS stimulant effects is what I call "anxiomimetic"—mimicking anxiety—and is adverse. This class has two main components. The first main anxiomimetic component is a stomach sensation just short of nausea. It feels as if I'm stuffed and need to brup, but can't. Anorexia may accompany this sensation, but it may not, because the percept also resembles the uncomfortable feeling of a stomach too long empty.

The other main anxiomimetic component is a pair of effects on the mind. One is distractibility, impairing concentration. Another is anhedonia, such that the pleasing effects of eating or orgasm are attenuated or abolished. The result is dysphoric.

The combined effects of the general stimulation and anixomimetic action are quite displeasing. Under their influence I will sometimes find myself eating nervously without enjoyment. The increased arousal and impulse for greater activity combine with the distractibility such that satisfaction is diminished. I can't concentrate enough to complete the tasks or thoughts to which I'm driven. Although this sort of arousal may be useful to someone who needs greater vigilance, otherwise it produces a scatterbrained effect, leading to ennui (boredom and annoyance).

The essential method of U.S. Pat. No. 3,161,650 had been used to condense erythro-(+/−)-norephedrine (phenylpropanolamine) with cyanogen bromide to form (+/−)-cis-2-amino-4-methyl-5-phenyl-2-oxazoline. This is also known as (+/−)-cis-4,5-dihydro-4-methyl-5-phenyl-2-oxazolamine, and, as related to an anorexiant drug, is also called cis-4-methylaminorex. The substituents at positions 4 and 5 are cis to each other, and racemic (+/−) to the oxazole ring.

On widely separated occasions I orally administered to myself this material as the hydrochloride salt at 0.25, 0.25, 0.32, and 0.50 mg per kg of body weight. Each administration produced maximal relief from nasal and sinus congestion (due to allergic rhinitis beginning in approximately one hour, and lasting approximately 12 hours, and noticeable decongestion beyond that period for some hours, depending on dose.

While central nervous system stimulation accompanied this relief, the effects were not of the anxiomimetic type. At 0.25 mg/kg, the degree of general stimulation (manifested as pacing, fidgeting, jaw clenching, and clonus) was no greater than the general run of such symptoms accompanying effective systemic decongestant or bronchodilator treatment. Adverse CNS effects which would have been pronounced from a 12 hour decongestant dose of pseudoephedrine or phenylpropanolamine were lacking with cis-4-methylaminorex. There was no impairment of concentration or dysphoria. To the contrary, others have reported improved concentration and euphoria at comparable doses, though these effects were noticed by me only at higher doses. There was no feeling of boredom or annoyance.

Profound anorexia was also experienced with cis-4-methyl-aminorex, but not accompanied by an unpleasant stomach feeling. Enjoyment of eating was not impaired. There was neither a revulsion to food nor a compulsion to cram it in.

The one adverse effect which appears to be greater with cis-4-methylaminorex than with other sympathomimetics is dryness of the mouth.

0.50 mg/kg produced more noticeable general stimulation, though still within the range of that accompanying therapy with other useful sympathomimetics. Also experienced was an expansive, euphoric feeling, maximal for 8 hours, and tapering over the next 20 hours. It was a feeling of creativity and interest. However, decongestant effect was not significantly greater, and there was a behavioral rebound such that I slept extra long the next two nights.

Some sympathomimetic properties of cis-2-amino-4-methyl-5-phenyl-2-oxazoline were known before the present invention. However, its utility as a nasal decongestant was not obvious. In particular, it took experimentation by and on a subject-investigator experienced with sympathomimetics, and sensitive to their adverse effects, and in need of nasal and sinus decongestion, to show the advantage of this agent in terms of the specificity of its CNS stimulant effects.

Therefore I claim as my invention:

1. The method of decongesting the nose and paranasal sinuses of humans and animals which comprises the systemic administration thereto of 0.25 mg of (+/−)-cis-2-amino-4-methyl-5-phenyl-2-oxazoline or its hydrochloride salt thereof per kg of body mass per 12 hour period.

2. The method of claim 1 which is administered to avoid uncomfortable stomach feelings accompanying use of other decongestants and anorexiants.

3. The method of use in claim 1 which is administered to avoid impairment of concentration accompanying use of other decongestants and anorexiants.

4. The method of use in claim 1 which is administered to avoid anhedonia accompanying use of other decongestants and anorexiants.

5. The method of use in claim 1 which is administered to avoid dysphoria accompanying use of other decongestants and anorexiants.